(12) United States Patent
Lahrman et al.

(10) Patent No.: US 9,201,017 B2
(45) Date of Patent: Dec. 1, 2015

(54) PHOTON DOPPLER VELOCIMETRY FOR LASER BOND INSPECTION

(75) Inventors: David F. Lahrman, Powell, OH (US); Richard D. Tenaglia, Colombus, OH (US)

(73) Assignee: LSP Technologies, Inc., Dublin, OH (US)

( * ) Notice: Subject to any disclaimer, the term of this patent is extended or adjusted under 35 U.S.C. 154(b) by 18 days.

(21) Appl. No.: 13/587,411

(22) Filed: Aug. 16, 2012

(65) Prior Publication Data

US 2014/0049773 A1    Feb. 20, 2014

(51) Int. Cl.
*G01N 21/00* (2006.01)
*G01N 21/84* (2006.01)

(52) U.S. Cl.
CPC .... *G01N 21/8422* (2013.01); *G01N 2021/8438* (2013.01); *G01N 2021/8472* (2013.01)

(58) Field of Classification Search
CPC ..... G01N 21/95; G01N 27/82; G01N 27/904; G01N 21/9501
USPC ........................................... 356/237.1–237.5
See application file for complete search history.

(56) References Cited

U.S. PATENT DOCUMENTS

2007/0091316 A1*  4/2007  Lal et al. ........................ 356/486
2008/0094608 A1*  4/2008  Holtkamp et al. ............ 356/28.5

* cited by examiner

*Primary Examiner* — Michael P Stafira
(74) *Attorney, Agent, or Firm* — Benesch, Friedland, Coplan & Aronoff LLP; Benjamen E. Kern; Christopher H. Bond

(57) ABSTRACT

Methods, systems, and apparatuses are disclosed for using Photon Doppler Velocimetry for laser bond inspection.

20 Claims, 5 Drawing Sheets

PHOTON DOPPLER VELOCIMETRY FOR LASER BOND INSPECTION

BACKGROUND

Bonded materials are used in a variety of structural applications. For example, adhesively bonded, laminated composite structures are increasingly being used in aircraft construction to reduce weight, reduce or eliminate the number of separate components, and improve fuel efficiency. The presence of material defects in a composite aircraft structure can lead to disastrous failure of the structure under flight loads. These defects may exist in the composite laminate itself, as well as in the adhesive bonds in the structure. The defects may arise as a result of damage during service, or in the original manufacturing process.

The growing ubiquity of composite structures has led to an increased need for techniques to evaluate the strength of the composite structures, including the adhesive bonds themselves, without damaging or destroying the composite structures. Conventional non-destructive evaluation ("NDE") techniques are useful when a gap, crack, or void is present in a bonded material. However, conventional NDE techniques do not adequately identify deficiencies, such as weak bonds or "kissing bonds," where materials bonded together are in contact but without adequate structural strength. These deficiencies can result from bond surface contamination, improperly mixed or outdated adhesives, and improper adhesive application.

Laser bond inspection ("LBI") is an NDE technique for testing the integrity of bonded materials and structures. LBI is a method that involves sending a precisely controlled dynamic stress wave through an adhesive bond of a composite structure. Generally speaking, and with reference to FIG. 1, LBI involves the deposition of laser energy at a first surface of a bonded material, generating a compressive stress wave. The compressive stress wave propagates through the bonded material, through a bond of interest, to a second surface of the bonded material, where the wave is reflected as a tensile wave (not shown). The tensile wave propagates back through the bonded material and, when it reaches the bond of interest, stresses the bond. The application of dynamic stress on the bonded material is low enough to have no effect on the integrity of the bonded material or the bond itself if the bond is sufficiently strong. However, if the bond is below a suitable strength, the tensile wave will cause the bond to fail (or will expose its non-bonded nature, in the case of a kissing bond).

The traditional instrument for capturing surface velocity of high speed targets, such as when bonds are disrupted during LBI, has been the Velocity Interferometer System for Any Reflector ("VISAR"). See, e.g., U.S. Pat. No. 6,848,321 (The Boeing Company), which is incorporated by reference herein in its entirety. However, VISAR instruments are expensive, relatively difficult to use, and require extensive care for proper optical alignment and light collection. More recently, electromagnetic acoustic transducers ("EMAT" gauges) have been used with success in LBI. See, e.g., U.S. Pat. No. 7,770,454 and U.S. Pat. App. Pub. No. 2008/0257048, now U.S. Pat. No. 8,156,811 (LSP Technologies, Inc.), both of which are incorporated herein by reference in their entireties. EMAT gauges are relatively inexpensive and versatile. However, EMAT gauges often must be placed close to the workpiece surface being tested and can be sensitive to the standoff distance. Furthermore, the workpiece generally must have an electrically conductive surface in order to ensure proper operation of the EMAT gauges, or an electrically conductive material must be applied to the surface. The application of an electrically conductive surface to the workpiece can be expensive and cumbersome.

What is needed is an economical, relatively high standoff, non-contact sensor for measuring rapid changes in surface velocity such as those measured by laser bond inspection.

SUMMARY

In one embodiment, a system for non-destructively inspecting a bond in a bonded article is provided, the system comprising: (1) a first laser operable to non-destructively inspect a bond in a bonded article; (2) a first laser beam delivery system operable to deliver the first laser to the bond in the bonded article; (3) a processing head (also known as an inspection head) operable connected to the first laser beam delivery system; and (4) a Photon Doppler Velocimetry ("PDV") system, the PDV system further comprising a second laser operable to perform photon doppler velocimetry on a surface of the bonded article, a splitter, and a circulator.

In another embodiment, a system for laser bond inspecting a bond in a bonded article is provided, the system comprising: (1) a first laser, the first laser operable to non-destructively inspect a bond in a bonded article and configured to deliver laser pulses having: (a) a pulse energy between about 5 J and about 45 J; (b) a wavelength of about 1054 nm; and (c) a pulse width of between about 100 ns and 300 ns, and further being configured to deliver the laser pulses in a low-high-low pulse energy sequence; (2) a first laser beam delivery system comprising at least one of: (a) one or more mirrors; (b) an articulated arm operatively connected to a processing head; and (c) a fiber optic operatively connected to a processing head; and (3) a PDV system, the PDV system further comprising a second laser operable to perform photon doppler velocimetry on a surface of the bonded article, a splitter, and a circulator.

In another embodiment, a system for inspecting a bond in a bonded article is provided, the system comprising: (1) a first laser operable to non-destructively inspect a bond in a bonded article and configured to deliver a first laser beam; (2) a processing head, the processing head configured to deliver the first laser beam to the bonded article and deliver a transparent overlay to the bonded article; and (3) a PDV sensor for detecting surface motion in the bonded article, wherein the PDV sensor further comprises a second laser operable to perform photon doppler velocimetry on a surface of the bonded article, and wherein the processing head and the PDV sensor are operatively connected.

In another embodiment, a method for non-destructive testing of a bond in a bonded article is provided, the method comprising: lasing a bonded article with a first laser, the first laser configured to non-destructively test a bond in a bonded article in a low-high-low pulse energy sequence, each pulse having a pulse energy of between about 5 J and about 45 J; and detecting surface motion in the bonded article using a PDV sensor, wherein the PDV sensor uses a second laser to detect surface motion in the bonded article.

BRIEF DESCRIPTION OF THE DRAWINGS

The accompanying figures, which are incorporated in and constitute a part of the specification, illustrate various example systems, methods, and results, and are used merely to illustrate various example embodiments.

DETAILED DESCRIPTION

Figure 1:
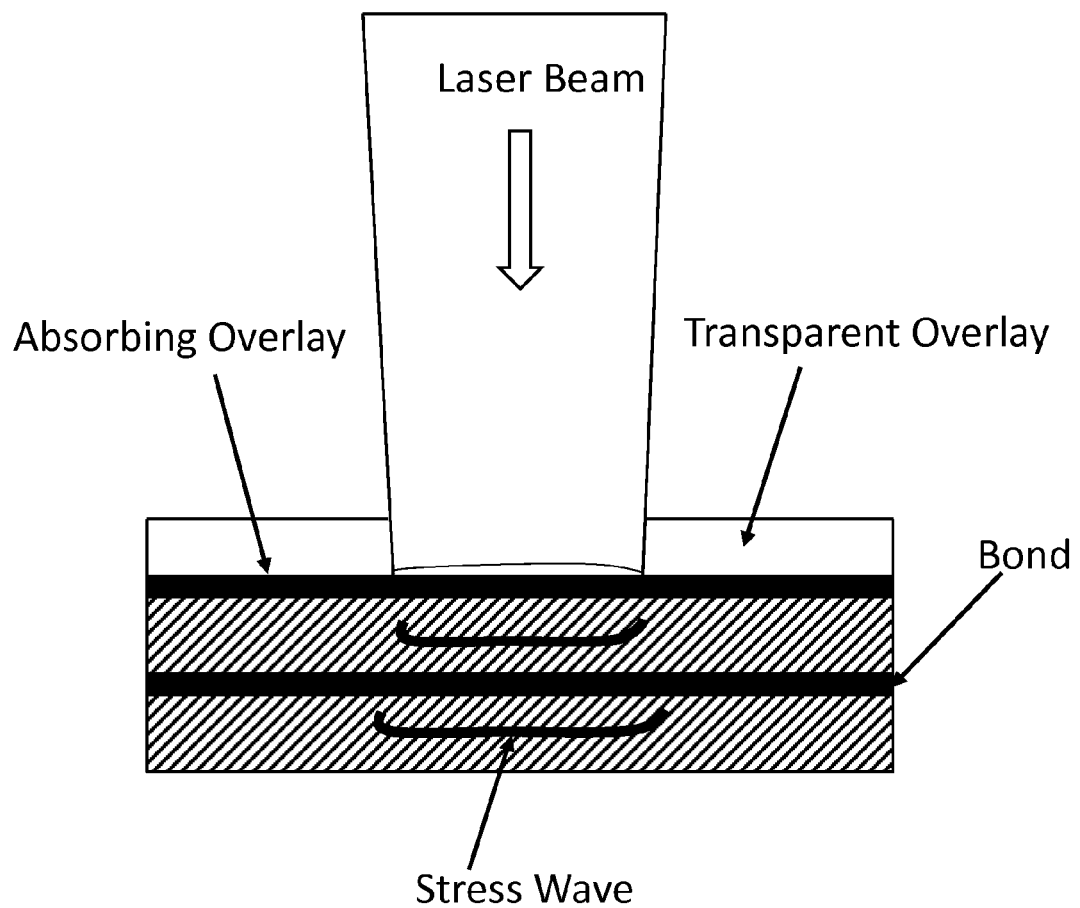
FIG. 1 illustrates a schematic of the initiation of the laser bond inspection process.
Figure 2:
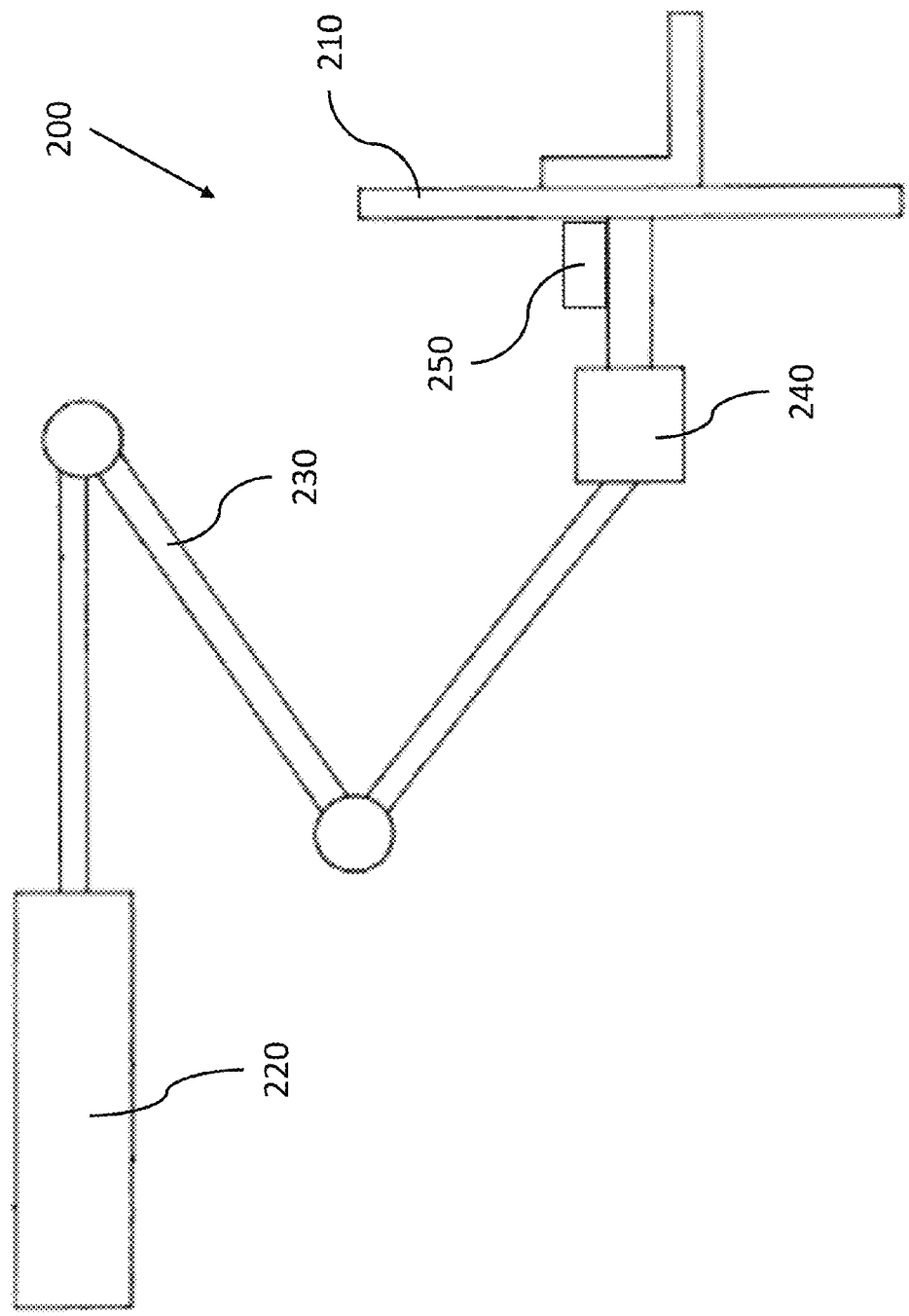
FIG. 2 illustrates an example arrangement of a laser bond inspection system.

The embodiments claimed herein disclose using a PDV sensor during LBI. With reference to FIG. 2, a system 200 for non-destructively inspecting a bond in a bonded article 210 is provided, system 200 comprising: a laser 220; a laser beam delivery system 230; a processing head 240; and a PDV sensor 250.

In one embodiment, laser 220 may be, for example, a neodymium:phosphate glass laser, such as, for example, those manufactured by LSP Technologies, Inc., a YAG laser, a YLF laser, or any other solid-state crystal material, in either a rod or a slab gain medium. Laser 220 may be configured to deliver laser pulses having a pulse energy of between about 5 J and about 45 J (at the output of the final amplifier module), a wavelength of about 1054 nm, and a pulse width of between about 100 ns and 300 ns, and further being configured to deliver the laser pulses in a low-high-low or probe-break-probe pulse energy sequence (i.e., a first laser pulse having a first energy, a second laser pulse having a second energy that is greater than the first energy but less than an energy required to break a properly constructed or "good" bond, and a third laser pulse having an energy which is approximately the same as the first pulse's energy), as described and illustrated in U.S. Pat. Nos. 7,770,454 and 8,156,811. Further configurations of laser 220 may include those described and illustrated in U.S. Pat. Nos. 7,770,454 and 8,156,811.

In one embodiment, laser beam delivery system 230 may comprise, for example, at least one of: (a) one or more mirrors; (b) an articulated arm; and (c) a fiber optic, and includes the laser beam delivery systems described and illustrated in U.S. Pat. Nos. 7,770,454 and 8,156,811. In one embodiment, where laser beam delivery system 230 is one or more mirrors, the beam may be directed to the surface of the bonded article without need for processing head 240. In alternative embodiments, where laser beam delivery system 230 is an articulated arm and/or a fiber optic, laser beam delivery system 230 may be operatively connected to processing head 240.

Processing head 240 may comprise a laser processing head similar to that disclosed in U.S. Pat. Nos. 7,770,454 and 8,156,811, except that instead of an EMAT gauge, a PDV sensor 250 is integrally disposed within the processing head.

The basic physics of PDV are as follows: A moving surface produces Doppler shifted light, which is recombined with the incident light signal to produce a beat frequency. This beat frequency is proportional to the velocity of the moving surface, and can be analyzed with modern digitizing equipment to yield velocity vs. time profiles with good accuracy.

With regard to data analysis, there are multiple methods available. In the time domain, the PDV system is treated as a displacement interferometer. In the frequency domain, the PDV system may be represented as a velocity interferometer. Accordingly, a Fourier Transform can be performed on the PDV raw data to analyze the beat frequency time history in order to generate velocity vs. time profiles.

Figure 3:
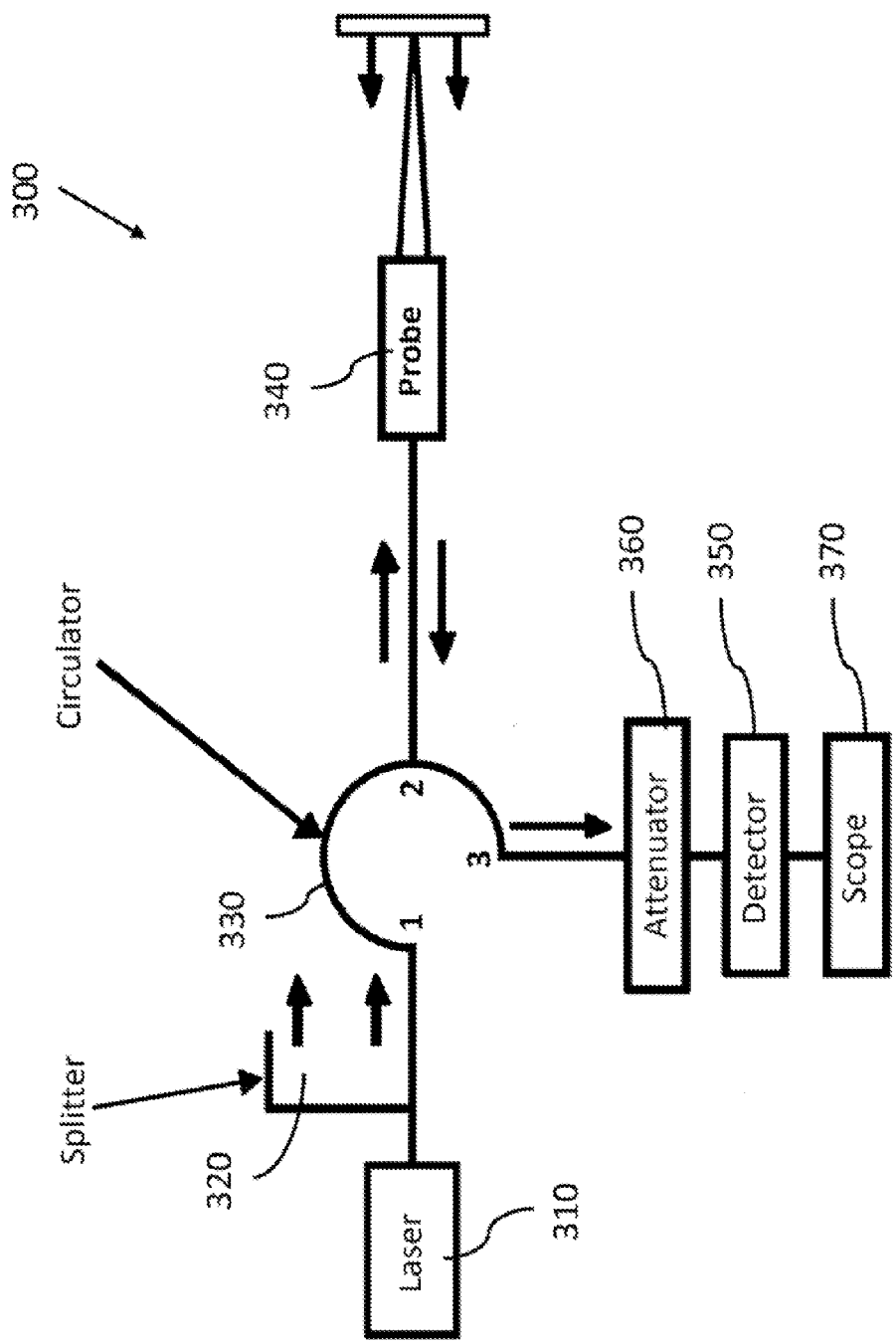
FIG. 3 illustrates an example PDV system.

FIG. 3 illustrates an example PDV system 300. PDV system 300 includes a laser 310. Laser 310 may be, for example, a high power erbium fiber laser having a narrow spectral line width. In one particular example, laser 310 may be a NP Photonics 1550 nm, 1000 mW output fiber laser with a line width of less than 3 kHz manufactured by NP Photonics, Inc. of Tucson, Ariz. PDV system 300 may also include a splitter 320, which divides laser 310's output into several fiber optic ports for multi-channel operations or phase comparison. PDV system 300 may also include a circulator 330, which may comprise a directional fiber optic device configured to guide light from laser 310 out to a probe 340, and reflected light from probe 340 to a detector 350. Probe 340 may be a collimating or focusing probe, optionally including a built-in reference partial reflection surface. Detector 350 may be, for example, a short rise time battery biased photodetector, having a high bandwidth. In one particular example, detector 350 may be a 1.5 GHz Newport detector manufactured by the Newport Corporation of Irvine, Calif. PDV system 300 may further include one or more attenuators 360. In one embodiment, attenuator(s) 360 are variable attenuators that allow for signal level adjustment and protection for detector 350 in the event of excessive optical flux. PDV system 300 may also include an oscilloscope 370. In one embodiment, oscilloscope 370 may be a 1 GHz, 5 GS/s, LeCroy Wavesurfer® 104MXs with four channels manufactured by the Teledyne LeCroy Corporation of Chestnut Ridge, N.Y. In one embodiment, oscilloscope 370 may have a relatively large amount of data storage at 10 Mpts on each channel. In one embodiment, storage for periods of up to 2 ms at full speed on each channel is possible.

Figure 4:
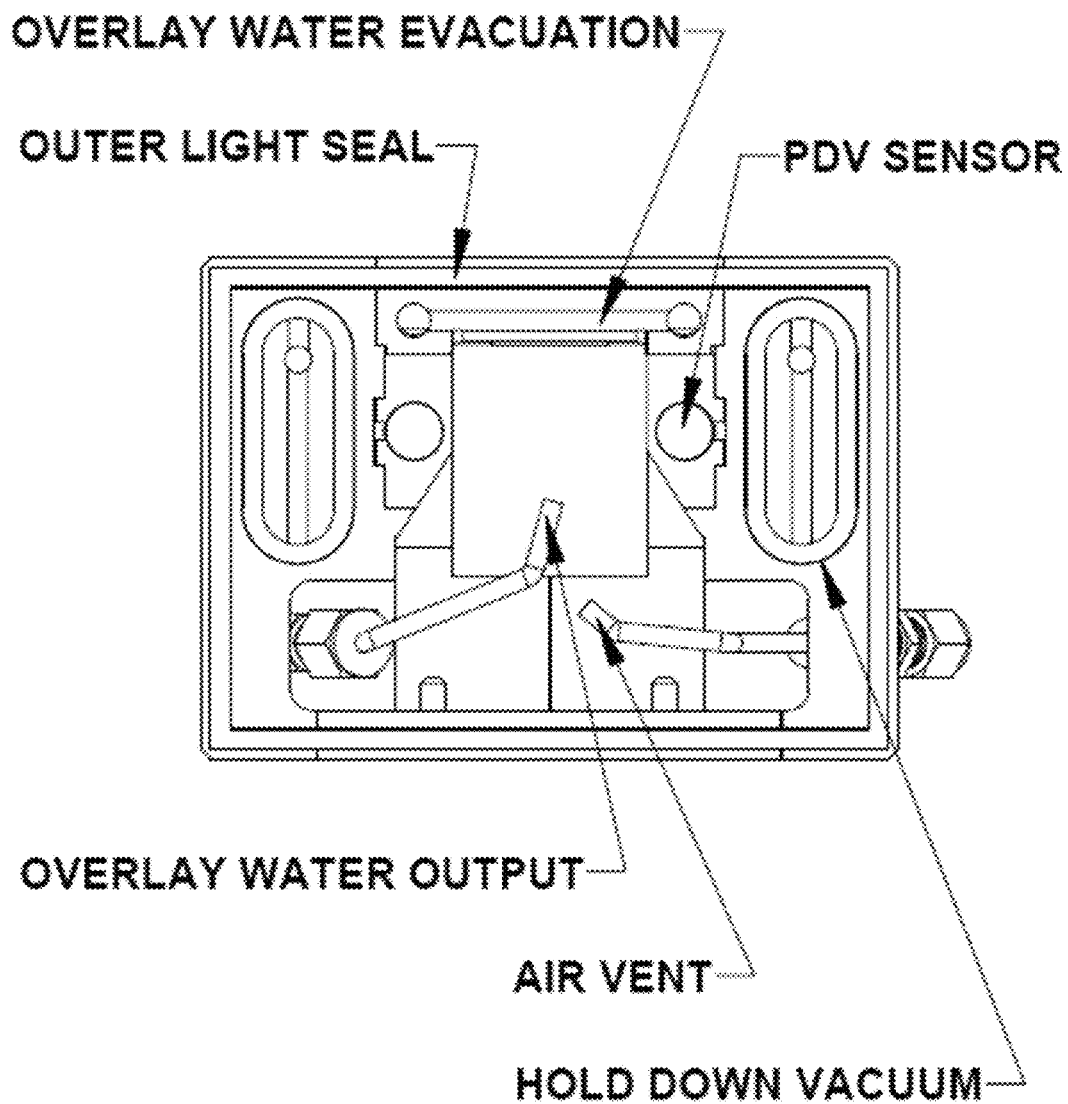
FIG. 4 illustrates an example laser processing head with an operatively connected PDV probe.

FIG. 4 illustrates an example laser processing head with an operatively connected PDV sensor.

In one embodiment, the system also includes ultrasonics for post-test analysis, as is known in the art. The ultrasonics may be integrated into the processing head, or the ultrasonics may be separate from any processing head.

Figure 5:
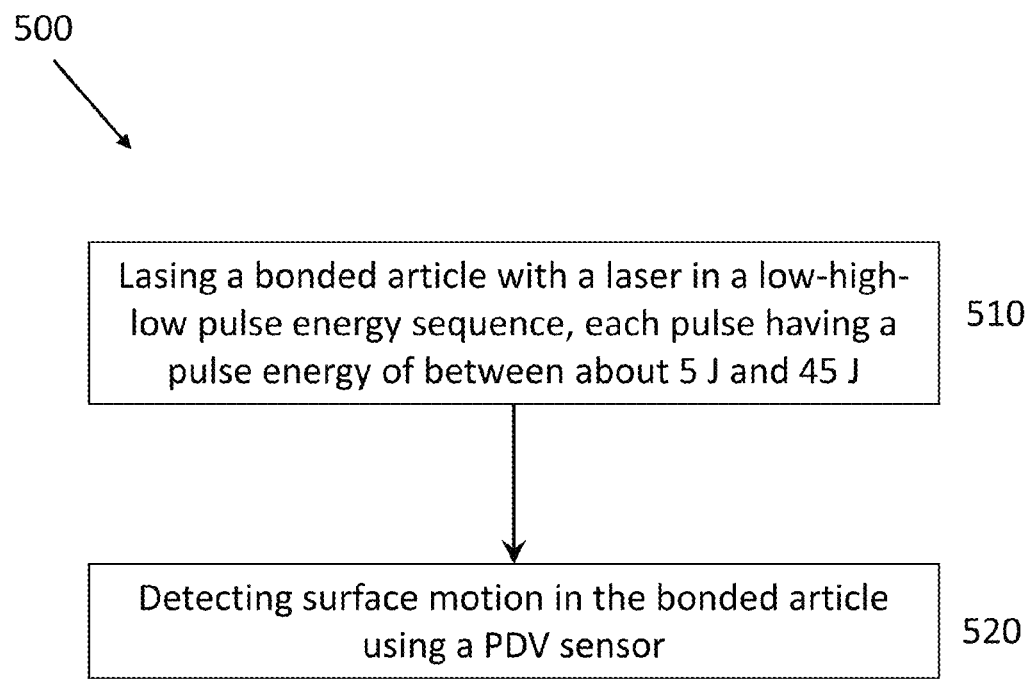
FIG. 5 is a flow chart of an example method for non-destructive testing of a bond in a bonded article.

Systems and apparatuses as described herein may be useful to non-destructively test a bond in a bonded article. FIG. 5 is a flow chart of a method 500 for non-destructive testing of a bond in a bonded article. In one embodiment, method 500 comprises: lasing a bonded article with a laser in a low-high-low pulse energy sequence, each pulse having a pulse energy of between about 5 J and about 45 J (510); and detecting surface motion in the bonded article using a PDV sensor (520).

Unless specifically stated to the contrary, the numerical parameters set forth in the specification, including the attached claims, are approximations that may vary depending on the desired properties sought to be obtained according to the exemplary embodiments. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Furthermore, while the systems, methods, and apparatuses have been illustrated by describing example embodiments, and while the example embodiments have been described and illustrated in considerable detail, it is not the intention of the applicants to restrict, or in any way limit, the scope of the appended claims to such detail. It is, of course, not possible to describe every conceivable combination of components or methodologies for purposes of describing the systems, methods, and apparatuses. With the benefit of this application, additional advantages and modifications will readily appear to those skilled in the art. Therefore, the invention, in its broader aspects, is not limited to the specific details and illustrative example and exemplary embodiments shown and described. Accordingly, departures may be made from such details without departing from the spirit or scope of the general inventive concept. Thus, this application is intended to embrace alterations, modifications, and variations that fall within the scope of the appended claims. The preceding description is not meant to limit the scope of the invention. Rather, the scope of the invention is to be determined by the appended claims and their equivalents.

To the extent that the term "includes" or "including" is employed in the detailed description or the claims, it is intended to be inclusive in a manner similar to the term "comprising," as that term is interpreted when employed as a transitional word in a claim. Furthermore, to the extent that the term "or" is employed in the claims (e.g., A or B) it is intended to mean "A or B or both." When the applicants intend to indicate "only A or B, but not both," then the term "only A or B but not both" will be employed. Similarly, when the applicants intend to indicate "one and only one" of A, B, or C, the applicants will employ the phrase "one and only one." Thus, use of the term "or" herein is the inclusive, and not the exclusive use. See Bryan A. Garner, A Dictionary of Modern Legal Usage 624 (2d. Ed. 1995).

Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. Finally, where the term "about" is used in conjunction with a number, it is intended to include ±10% of the number. In other words, "about 10" may mean from 9 to 11.

What is claimed is:

1. A system for non-destructively inspecting a bond in a bonded article, the system comprising:
   (1) a first laser operable to non-destructively inspect a bond in a bonded article;
   (2) a first laser beam delivery system operable to deliver the first laser to the bond in the bonded article;
   (3) a processing head operatively connected to the first laser beam delivery system; and
   (4) a PDV system, the PDV system further comprising a second laser operable to perform photon doppler velocimetry on a surface of the bonded article, a splitter, and a circulator.

2. A system for laser bond inspecting a bond in a bonded article, the system comprising:
   (1) a first laser, the first laser operable to non-destructively inspect a bond in a bonded article and configured to deliver laser pulses having:
      (a) a pulse energy between about 5 J and about 45 J;
      (b) a wavelength of about 1054 nm; and
      (c) a pulse width of between about 100 ns and 300 ns, and further being configured to deliver the laser pulses in a low-high-low pulse energy sequence;
   (2) a first laser beam delivery system operable to deliver the first laser and comprising at least one of:
      (a) one or more mirrors;
      (b) an articulated arm operatively connected to a processing head; and
      (c) a fiber optic operatively connected to a processing head; and
   (3) a PDV system, the PDV system further comprising a second laser operable to perform photon doppler velocimetry on a surface of the bonded article, a splitter, and a circulator.

3. A system for laser bond inspecting a bond in a bonded article, the system comprising:
   (1) a first laser operable to non-destructively inspect a bond in a bonded article and configured to deliver a first laser beam;
   (2) a processing head, the processing head configured to deliver the first laser beam to the bonded article and deliver a transparent overlay to the bonded article; and
   (3) a PDV sensor for detecting surface motion in the bonded article, wherein the PDV sensor further comprises a second laser operable to perform photon doppler velocimetry on a surface of the bonded article, and wherein the processing head and the PDV sensor are operatively connected.

4. A method for non-destructive testing of a bond in a bonded article, the method comprising:
   lasing a bonded article with a first laser, the first laser configured to non-destructively test a bond in a bonded article in a low-high-low pulse energy sequence, each pulse having a pulse energy of between about 5 J and about 45 J; and
   detecting surface motion in the bonded article using a PDV sensor, wherein the PDV sensor uses a second laser to detect surface motion in the bonded article.

5. The system of claim 1, wherein the first laser is configured to deliver a laser pulse having a pulse energy between about 5 J and about 45 J.

6. The system of claim 1, wherein the first laser is configured to deliver a laser pulse having a pulse energy with a wavelength of about 1,054 nm.

7. The system of claim 1, wherein the first laser is configured to deliver a laser pulse having a pulse width of between about 100 ns and 300 ns, and further being configured to deliver the laser pulses in a low-high-low pulse energy sequence.

8. The system of claim 1, wherein the first laser beam delivery system comprises at least one of: one or more mirrors; an articulated arm operatively connected to a processing head; and a fiber optic operatively connected to a processing head.

9. The system of claim 1, wherein the PDV system is operatively connected to the processing head.

10. The system of claim 1, wherein the system further comprises ultrasonics.

11. The system of claim 10, wherein the ultrasonics are integrated into the processing head.

12. The system of claim 1, wherein the second laser has a wavelength of about 1,550 nm.

13. The system of claim 1, wherein the second laser is a high power erbium laser with a narrow spectral linewidth.

14. The system of claim 13, wherein the second laser is a fiber laser with an output of about 1,000 mW and line width of less than about 3 kHz.

15. The system of claim 1, wherein the splitter divides the second laser into two or more fiber optic ports for multi-channel operations and phase comparison.

16. The system of claim 1, wherein the circulator further comprises a directional fiber optic device configured to: (1) guide light from the second laser to a probe; and (2) guide reflected light from the probe to a detector.

17. The system of claim 16, wherein the probe is at least one of: a collimating probe and a focusing probe.

18. The system of claim 1, wherein the PDV system further comprises one or more attenuators.

19. The system of claim 1, wherein the PDV system further comprises an oscilloscope.

20. The method of claim 4, the method further comprising analyzing data for the detected surface motion in at least one of: a time domain and a frequency domain.

* * * * *